US006663837B1

United States Patent
Belmont

(10) Patent No.: US 6,663,837 B1
(45) Date of Patent: Dec. 16, 2003

(54) HOUSING BOX FOR ELECTRONIC CHIP WITH BIOLOGICAL PROBES

(75) Inventor: Andre Belmont, La Batie Divisin (FR)

(73) Assignee: Mesatronic, Saint Jean de Moirans (FR)

( * ) Notice: Subject to any disclaimer, the term of this patent is extended or adjusted under 35 U.S.C. 154(b) by 0 days.

(21) Appl. No.: 09/807,901

(22) PCT Filed: Oct. 20, 1999

(86) PCT No.: PCT/FR99/02553

§ 371 (c)(1),
(2), (4) Date: Apr. 19, 2001

(87) PCT Pub. No.: WO00/23617

PCT Pub. Date: Apr. 27, 2000

(30) Foreign Application Priority Data

Oct. 20, 1998 (FR) .............................. 98 13339

(51) Int. Cl.[7] .................. B01L 9/00; G01N 21/00; G01N 15/06; C12M 1/34; C12M 3/00

(52) U.S. Cl. .................. 422/104; 422/50; 422/55; 422/58; 422/68.1; 422/82.05; 422/102; 422/103; 435/287.1; 435/287.2

(58) Field of Search ................ 422/102, 103, 422/104, 50, 55, 58, 68.1, 82.05; 435/287.2, 287.1

(56) References Cited

U.S. PATENT DOCUMENTS 5,143,854 A 9/1992 Pirrung et al.
5,436,129 A * 7/1995 Stapleton .................. 435/6
5,605,662 A 2/1997 Heller et al.
6,465,241 B2 * 10/2002 Haronian et al. ........ 435/287.2
6,551,841 B1 * 4/2003 Wilding et al. ............. 436/518

FOREIGN PATENT DOCUMENTS

| WO | WO 91/15595 | 10/1991 |
| WO | WO 92/10092 | 6/1992 |
| WO | WO 95/33846 | 12/1995 |
| WO | WO 96/07917 | 3/1996 |

* cited by examiner

Primary Examiner—Jill Warden
Assistant Examiner—Brian Sines
(74) Attorney, Agent, or Firm—Oliff & Berridge, PLC

(57) ABSTRACT

The invention concerns a housing box for an electronic chip with biological probes, comprising a flat support device formed by assembling a first lower support and a second upper support, whereof one is equipped with a connector for activating the chip, a plurality of electrical connections extending along the assembly interface and cooperating with electrical connecting means ensuring the continuity of the electrical connections with the chip strip conductors. Protective means are placed in the environment of the chip to obtain an electrical and biological insulating effect for the active part with respect to the input and output contacts of the connector. The invention is useful for molecular analysis, in particular of DNA or any other biological reaction.

13 Claims, 3 Drawing Sheets

HOUSING BOX FOR ELECTRONIC CHIP WITH BIOLOGICAL PROBES

BACKGROUND OF THE INVENTION

The invention relates to a housing box for an electronic chip with biological probes, in particular for molecular analysis of DNA, said box comprising a flat support device provided with a window for access to a matrix of electrodes forming the active part of the chip.

STATE OF THE ART

A DNA chip is formed by a silicon substrate whereon one or a plurality of sequence(s) of biological probes formed by a matrix of electrodes and counter-electrodes each having small dimensions, about 50×50 microns, is(are) deposited. The arrangement of the probes at particular points of the substrate is performed according to known processes described in the documents U.S. Pat. No. 5,143,854 and WO 92/10092.

Each probe is moreover addressable by an electronic demultiplexing circuit integrated in the substrate so that the set of points of the matrix constitutes the image of a multitude of known DNA sequences relative to specific types of viruses. When molecular analysis is performed, the solution containing the patient's DNA is deposited on the chip, and chemical bonds revealed by a fluorescence effect then form at certain points of the substrate.

It has been proposed according to the document WO 95/33846 to integrate a DNA chip in an enclosure formed by a flat support equipped with a cavity for access to the electrode matrix. The chip is generally stuck to the support by an adhesive, for example silicone or a cement, and the liquid (pyrrol-base reactive agent) and the DNA to be tested simply have to be inserted in the cavity to perform the analysis.

OBJECT OF THE INVENTION

The object of the invention is to achieve an electrical connection between the biological chip and a connecting device accessible on the box and to obtain optimum protection of the chip with respect to a given environment.

The electronic chip housing box according to the invention is characterized in that:
  the support device is formed by assembly of a first lower support and a second upper support, one whereof is equipped with a connector for activation of the chip,
  a plurality of electrical connections extend along the assembly interface of the first and second supports between the connector and the chip,
  electrical connecting means are arranged to ensure the continuity of the electrical connections with conducting strips of the chip,
  and protective means are placed in the environment of the chip to obtain an electrical and biological insulating effect of the active part with respect to the input and output contacts of the connector.

According to one feature of the invention, the contacts of the connector and the electrical connections are made on one of the supports by means of a printed circuit or a conducting screen printing. It is also possible to use a flexible flat jumper added-on to one of the supports.

According to another feature of the invention, the electrical connecting means between the electrical connections and the chip are achieved either by soldering a conducting wire, or by melting a fusible tin-lead pad onto the chip, or by interposing double-sided adhesive strips made of conducting elastomer material.

According to a first embodiment, the box is characterized in that in that:
  the connector and the electrical connections are located with the chip on the first lower support of the box,
  the chip protrudes into the window arranged in the second upper support, which presents larger dimensions than the chip,
  and a resin-base protective layer is deposited in said window to completely cover the electrical connecting means and the empty part of the cut-out surrounding the periphery of the chip.

According to a second embodiment, the box is characterized in that in that:
  the connector and the electrical connections are arranged on the second upper support, which support is provided with the window having a smaller dimension than the chip,
  the first lower support is equipped with a groove for housing the chip, the thickness of said chip being smaller than the depth of said groove,
  and a bridging gap is arranged between the chip and the first support to receive a seal and electrical connecting means.

According to one feature of the invention, a visualization prism is advantageously incorporated in the window to divert an incident reading laser beam in a parallel direction above the probes of the chip.

The box houses a plurality of chips accessible via a single window and connected to a single connector. The chips can be integrated in a semi-conducting substrate.

BRIEF DESCRIPTION OF THE DRAWINGS

Other advantages and features will become more clearly apparent from the following description of an embodiment of the invention given as a non-restrictive example only and illustrated in the accompanying drawings in which.

DESCRIPTION OF SEVERAL PREFERRED EMBODIMENTS

Figure 1:
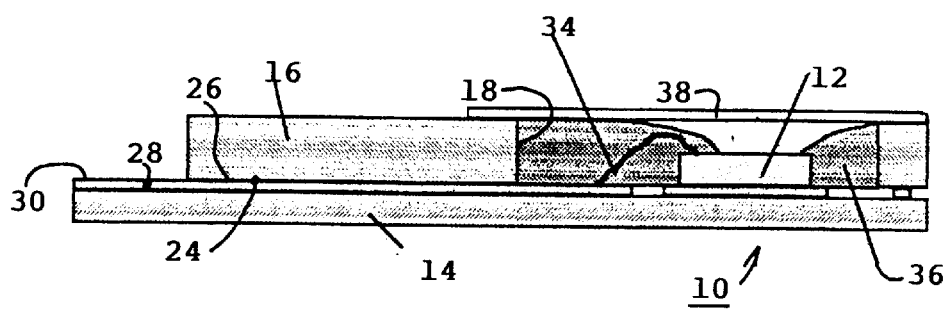
FIG. 1 is a cross-section view of a housing box of an electronic chip according to the invention.
Figure 2:
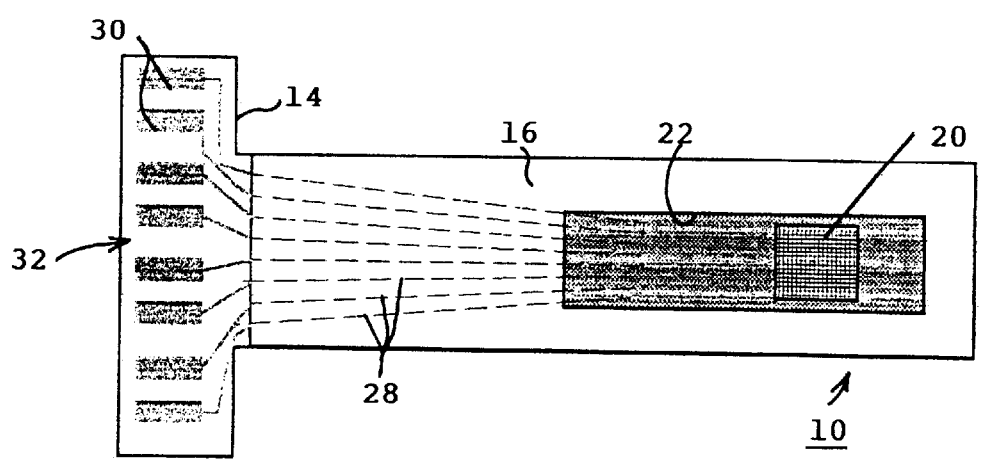
FIG. 2 is an outline view of the box of FIG. 1.

With reference to FIGS. 1 and 2, a box 10 housing a biological DNA chip 12 comprises a first lower support 14 on which support the chip 12 is stuck, and a second upper support 16 provided with a window 18 for access to the active face 20 of the chip 12. The window 18 is formed by a rectangular cut-out 22 passing through the whole thickness of the second support 16 and presenting a larger surface than that of the chip 12.

The active face 20 of the chip 12 comprises a matrix of metallic electrodes, in particular made of gold, arranged at particular points of the silicon substrate to form the different biological probes.

The adjoinment face 24 of the first lower support 14 with the adjacent internal face 26 of the second upper support 16 is provided with a plurality of electrical connections 28 extending along the assembly interface of the supports 14, 16 and connected to contacts 30 of a connector 32 arranged at the end of the first lower support 14. The electrical connections 28 and the contacts 30 of the connector 32 on the first support 14 can be achieved by different known processes, using in particular the printed circuit technology, screen printing, or an add-on flexible flat jumper. The second upper support 16 with the window 18 covers the adjoinment face 24 of the first support 14, except at the location of the connector 32 which remains accessible with the active surface 20 receiving the reactive liquid and the DNA to be examined.

Opposite the connector 32, the ends of the electrical connections 28 are positioned inside and at the back of the window 18, and are connected to conducting strips arranged on the active face 20 of the chip 12 by electrical connecting means 34. In FIG. 1, these electrical connecting means 34 are achieved by ultrasonic soldering of an aluminium or gold conducting wire. This bonding operation can naturally be replaced by other processes according to the technology of the chip 12.

Sealing is achieved by means of a protective layer 36 of thermosetting resin placed in the window 18 until it overlaps the edges of the chip 12, so as to completely coat the electrical connecting means 34 and the empty part of the cut-out 22 surrounding the periphery of the chip 12. The material of the protective layer 36 is an-electrical insulator and has biological properties which are neutral or compatible with pyrrol. This results in an electrical and biological insulating effect of the active part 20 of the chip 12 with respect to the input and output contacts 30 of the connector 32.

The second upper support 16 with the window 18 is advantageously covered by a glass plate 38 designed to facilitate receipt and transmission of signals when biological analysis is performed.

Figure 3:
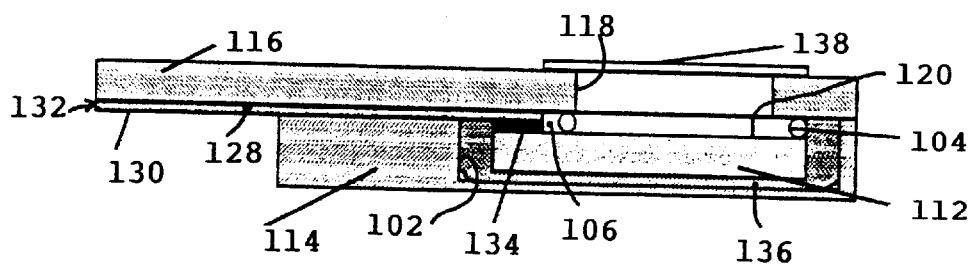
FIGS. 3 and 4 represent identical views to FIG. 1 of two alternative embodiments.

In the alternative embodiment of FIG. 3, the box 100 comprises a first lower support 114 equipped with a groove 102 in which groove the biological DNA chip 112 is housed, the thickness of the chip 112 being smaller than the depth of the groove 102. A second upper support 116 covers the whole surface of the first lower support 114, and is provided with a window 118 arranged facing the active part 120 of the chip 112. The size of the window 118 is in this case smaller than that of the chip 112.

The electrical connections 128 connected to the contacts 130 of the connector 132 are arranged on the second upper support 116 and extend up to inside the groove 102, being separated from the chip 112 by a bridging gap 106 having a small thickness.

The electrical connecting means 134 between the electrical connections 128 and the chip 112 are achieved for example by the "flip-chip" process consisting in melting a fusible tin-lead pad, fixedly secured to the electrical contact, onto the chip. It is also possible to make use of double-sided adhesive strips made of conducting elastomer material, the thickness of the strips corresponding to the bridging gap. In the case of chips with vias, the electrical contact can be made on the opposite face from the active part 120.

Sealing of the active part 120 is achieved by means of a seal 104 of slightly larger size than that of the window 118 and inserted between the chip 112 and the second upper support 116 facing the window 118. The material of the seal 104 is chosen to be biologically compatible with pyrrol. It is also possible to achieve sealing by injecting a polymerizable and biologically compatible resin into the gap 106.

The protective layer 136 is housed in the groove 102 and surrounds the lateral edges and the bottom face of the chip 112 opposite the active part 120. The glass plate 138 covers the window 118 as in the case of FIG. 1.

After the chip 12, 112 has been encapsulated in the respective box 10, 100, the active part 20, 120 remains accessible for deposition of the pyrrol-base liquid with the DNA to be tested, while guaranteeing the electrical and biological insulation thereof with respect to the contacts 30, 130 of the respective connector 32, 132.

Figure 4:
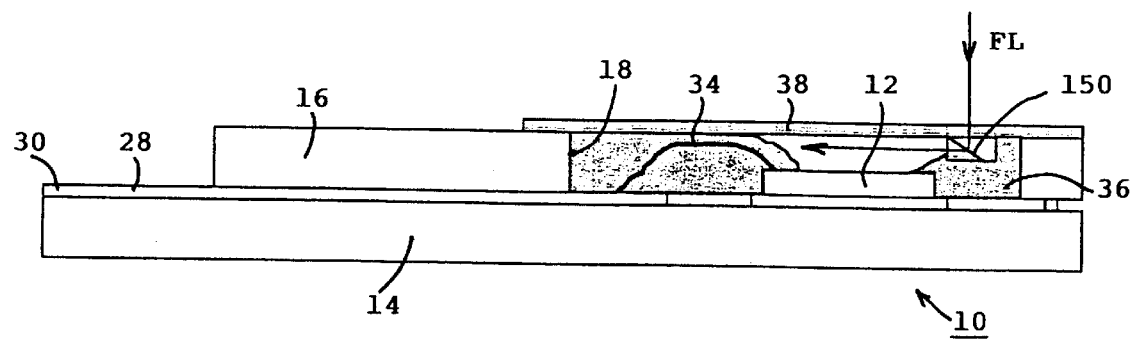

In FIG. 4, the box 10 in addition contains a visualization prism 150 designed to divert a reading laser beam FL directed perpendicularly to the glass plate 38. The prism 150 is arranged in the window 18 between the protective layer 36 and the internal face of the glass plate 38. The hypotenuse of the prism 150 diverts the incident laser beam FL in a parallel direction above the probes of the chip 12. Incorporating the prism 150 under the glass plate 38 improves reading of the biological analysis when receipt and transmission of the laser beam take place.

Figure 5:
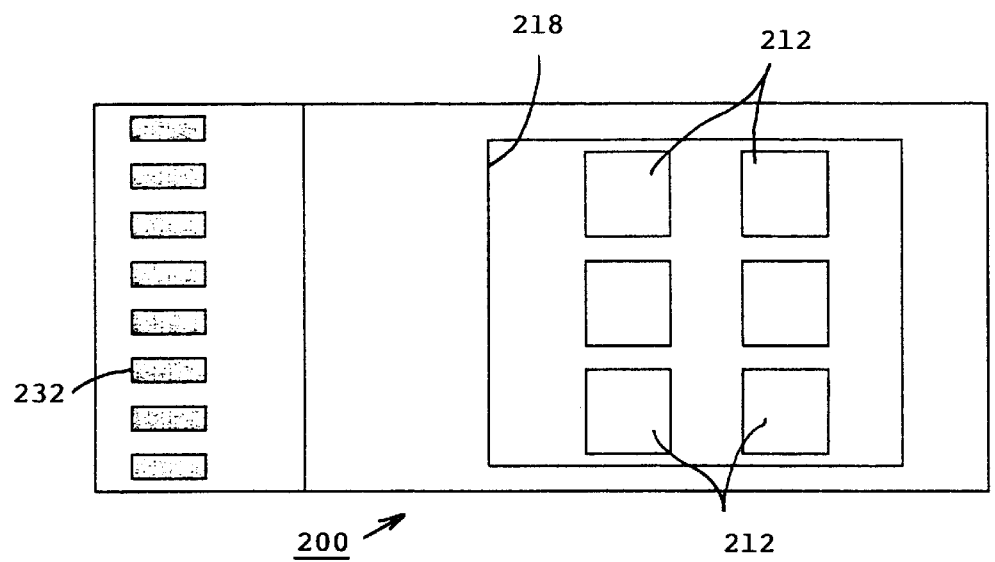
FIG. 5 is an outline view of a multiple chip box.

According to FIG. 5, a window 218 gives access to several biological DNA chips 212 incorporated in a single box 200 to increase the number of probes. Electrical connections (not represented) connect the different chips 212 to the same connector 232.

Figure 6:
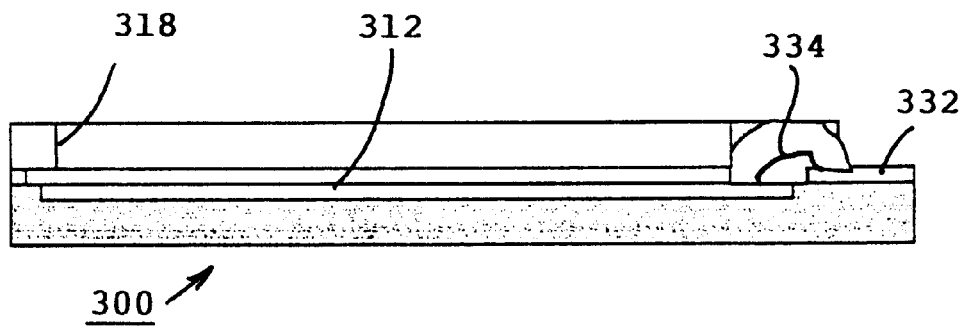
FIG. 6 shows a cross-section view of a box housing a substrate.
Figure 7:
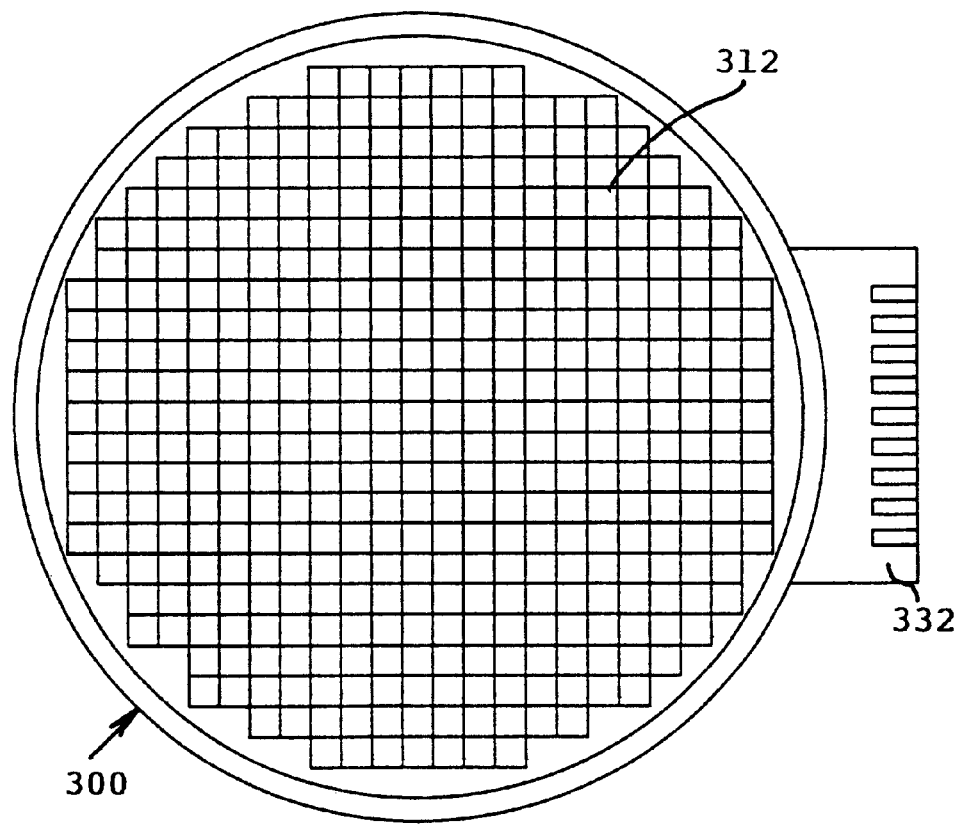
FIG. 7 is an outline view of FIG. 6.

With reference to FIGS. 6 and 7, the multiple-chip system according to FIG. 5 can be extrapolated to a complete substrate. A box 300 of cylindrical shape acts as housing for the semi-conducting substrate 312 accessible via a cylindrical window 318 and connected to the connector 332 by electrical connections 334.

What is claimed is:

1. A housing box for an electronic chip with biological probes, in particular for molecular analysis of DNA, said box comprising a flat support device provided with a window for access to a matrix of electrodes forming the active part of the chip, wherein:

the support device is formed by assembly of a first lower support and a second upper support, and being equipped with a connector having input and output contacts for activation of the chip, the first lower support and the second upper support forming an assembly interface a plurality of electrical connections extending along the assembly interface of the first lower support and the second upper supports between the connector and the chip, electrical connecting means connecting the plurality of electrical connections with conducting strips of said chip, and protective means adjacent the chip to obtain an electrical and biological insulating effect of the active part with respect to the input and output contacts of the connector and wherein the window is adjacent the second upper support.

2. The housing box for the electronic chip with biological probes according to claim 1, wherein the input and output contacts of the connector and the plurality of electrical connections are made on one of the supports by means of a printed circuit or a conducting screen printing.

3. The housing box for the electronic chip with biological probes according to claim 1, wherein the plurality of electrical connections are a flexible flat jumper added-on to one of the supports.

4. The housing box for the electronic chip with biological probes according to claim 1, wherein the electrical connecting means comprise a conducting wire.

5. The housing box for the electronic chip with biological probes according to claim 1, wherein the electrical connecting means comprise a fused tin-lead pad, fixedly secured to the end of the plurality of electrical connections onto the chip.

6. The housing box for the electronic chip with biological probes according to claim 1, wherein the electrical connecting means are obtained by interposing double-sided adhesive strips made of conducting elastomer material.

7. The housing box for the electronic chip with biological probes according to claim 1, wherein:

the connector and the plurality electrical connections are located with the chip on the first lower support of the box, the second upper support has a window therein.

the chip is arranged in the window arranged in the second upper support, the second upper support having larger dimensions than the chip, and a resin-base protective layer is deposited in said window in the second upper support to completely cover the electrical connecting means and an empty area surrounding the periphery of the chip.

8. The housing box for the electronic chip with biological probes according to claim 7, wherein the material of the protective layer is an electrical insulator and has biological properties which are neutral or compatible with the pyrrol-base reactive agent.

9. The housing box for the electronic chip with biological probes according to claim 1, wherein:

the connector and the plurality of electrical connections are arranged on the second upper support, the second upper support is provided with the window having a smaller dimension than the chip, the first lower support is equipped with a groove for housing the chip, the thickness of said chip being smaller than the depth of said groove, and a bridging gap is arranged between the chip and the first lower support to receive a seal and the electrical connecting means.

10. The housing box for the electronic chip with biological probes according to claim 9, wherein the material of the seal is biologically compatible with pyrrol, and a resin-base protective layer is housed in the groove and surrounds the lateral edges and the bottom face of the chip opposite the active part.

11. The housing box for the electronic chip with biological probes according to claim 1, wherein a window is formed in the second upper support and a visualization prism is incorporated in the window to divert an incident reading laser beam in a parallel direction above the probes of the chip.

12. The housing box according to claim 1, housing a plurality of chips accessible via a single window and connected to a single connector.

13. The housing box according to claim 12, wherein the chips are integrated in a semi-conducting substrate connected to a connector.

* * * * *